(12) United States Patent
Maillard et al.

(10) Patent No.: US 9,932,337 B2
(45) Date of Patent: Apr. 3, 2018

(54) METHOD FOR THE PRODUCTION OF PRAZIQUANTEL AND PRECURSORS THEREOF

(71) Applicant: Merck Patent GmbH, Darmstadt (DE)

(72) Inventors: David Maillard, Darmstadt (DE); Andreas Waechtler, Darmstadt (DE); Jeremy Maurin, Lieuran-Cabrieres (FR); Ewgenij Wakaresko, Fischbachtal (DE); Christian Jasper, Seligenstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/528,116

(22) PCT Filed: Nov. 19, 2015

(86) PCT No.: PCT/EP2015/002316
§ 371 (c)(1),
(2) Date: May 19, 2017

(87) PCT Pub. No.: WO2016/078765
PCT Pub. Date: May 26, 2016

(65) Prior Publication Data
US 2017/0320873 A1 Nov. 9, 2017

(30) Foreign Application Priority Data

Nov. 21, 2014 (EP) ..................................... 14003933

(51) Int. Cl.
| | | |
|---|---|---|
| *C07D 487/04* | (2006.01) | |
| *C07D 471/04* | (2006.01) | |
| *C07D 217/14* | (2006.01) | |
| *C07C 59/64* | (2006.01) | |
| *C07C 59/84* | (2006.01) | |

(52) U.S. Cl.
CPC ............ *C07D 471/04* (2013.01); *C07C 59/64* (2013.01); *C07C 59/84* (2013.01); *C07D 217/14* (2013.01); *C07B 2200/07* (2013.01)

(58) Field of Classification Search
CPC .. C07D 487/04; C07D 471/04; C07D 217/14; C07C 59/64; C07C 59/84
USPC ........................................................ 544/344
See application file for complete search history.

(56) References Cited

PUBLICATIONS

International Search Report dated Feb. 8, 2016 issued in corresponding PCT/EP2015/002316 application (3 pages).
Written Opinion of the International Searching Authority dated Feb. 8, 2016 issued in corresponding PCT/EP2015/002316 application (5 pages).
A. Cedillo-Cruz et al., "A Straightforward and Efficient Synthesis of Praziquantel Enantiomers and Their 4'-Hydroxy Derivatives", Tetrahedron Asymmetry, vol. 25, No. 2 (2014) pp. 133-140.
M. Woelfle et al., "Resolution of Praziquantel", PLOS—Neglected Tropical Diseases, vol. 5, Issue 9 (Sep. 2011) pp. 1-7.

*Primary Examiner* — Venkataraman Balasubramanian
(74) *Attorney, Agent, or Firm* — Millen White Zelano and Branigan, PC; Csaba Henter (57) ABSTRACT

The present invention relates to methods for the production of enantiopure or enantioenriched Praziquantel precursors and to methods for the production of enantiopure or enantioenriched Praziquantel comprising the methods for the production of the Praziquantel precursors. The present invention further relates to compounds or intermediates useful in such methods.

20 Claims, 1 Drawing Sheet

METHOD FOR THE PRODUCTION OF PRAZIQUANTEL AND PRECURSORS THEREOF

FIELD OF THE INVENTION

The present invention relates to methods for the production of the enantiopure or enantioenriched Praziquantel precursors and to methods for the production of enantiopure or enantioenriched Praziquantel comprising the methods for the production of the Praziquantel precursors. The present invention further relates to compounds or intermediates useful in such methods.

BACKGROUND OF THE INVENTION

The anthelmintic Praziquantel has been registered, approved and commercialized in the beginning of the 80's of the last century as a racemate. However, the active molecule (eutomer) is the (R)-enantiomer (P. Andrews, H. Thomas, R. Pohlke, J. Seubert Medical Research Reviews 3, 147(1983)).

The racemic Praziquantel has a repugnantly bitter taste. This leads to acceptance issues—in particular in the treatment of young children. The (R)-Praziquantel eutomer is considered to have a less bitter taste than the (S)-Praziquantel distomer (T. Meyer et al. (2009) PLoS Negl Trop Dis 3(1): e357). Thus, there is a strong demand for a cost efficient manufacturing process for enantiomerically pure (R)-Praziquantel.

Many efforts were spent in the last decades to develop a manufacturing process for (R)-Praziquantel or its analogues. These processes can be divided in two groups, firstly enantioselective synthesis routes and secondly methods using a racemic process in combination with a chiral resolution. So far, a few enantioselective processes have been reported, but all of them are laborious and costly.

Woelfle et al. describe a chiral resolution of the Praziquantel precursor Praziquanamine (1,2,3,6,7,11b-Hexahydropyrazino[2,1-a]isoquinolin-4-one) by (−)-dibenzoyl-L-tartaric acid (Resolution of Praziquantel, M. Woelfle, J-P. Seerden, J. de Gooijer, Krees Pouwer, P. Olliaro, M. H. Todd, (2011) PLoS Negl. Trop. Dis 5(9):e1260.doi:10.1371/journal.pntd.000260). This resolution achieves rather low yields due to the fact that two crystallization steps are necessary to reach sufficiently high optical purity. Another problem associated with this procedure is the laborious and time-consuming recycling of (S)-Praziquanamine which could be done using the sequence: acylation, oxidative dehydrogenation, hydrogenation and finally deacylation. Beside this, the recycling of (−)-dibenzoyl-L-tartaric acid causes problems, because it is prone to saponification and trans-esterification. Both aspects are particularly difficult on production scale.

Alberto Cedillo Cruz et al. Tetrahedron: Asymmetry (2014), 25(2), 133-140 describes a chromatographic separation of the diastereomers Naproxen-(R)/(S)-Praziquanamide, ((11bS)- and (11bR)-[2S)-2-(6-Methoxy-2-naphthalenyl)-1-oxopropyl]-1,2,3,6,7,11b-hexahydro-2-4H-pyrazino[2,1-a]isoquinolin-4-one which are synthesized from (S)-Naproxen-acidchloride and racemic Praziquanamine, on an achiral phase. In order to obtain the (R)-Praziquanamine the covalent bond in (11bR)-[2S)-2-(6-Methoxy-2-naphthalenyl)-1-oxopropyl]-1,2,3,6,7,11b-hexahydro-2-4H-pyrazino[2,1-a]isoquinolin-4-one must be cleaved under drastic conditions (85%-phosphoric acid, 150° C.). This process is laborious and not economic. Further there is no efficient recycling of the undesired (S)-Praziquanamine.

DESCRIPTION OF THE INVENTION

It is an object of the present invention to provide an efficient method for the chiral resolution of a racemic Praziquantel precursor (in particular Praziquanamine and N-{[(1R)-1,2,3,4,tetrahydro-1-isoquinolin-1-yl]methyl}acetamide (in the following Praziquanacetamide)), which works reliably even on large scale and which can be utilized in a method for the production of enantiopure or enantioenriched (R)-Praziquantel.

This object has surprisingly been solved by a method for the production of enantiopure or enantiomerically enriched (R)-Praziquanamine comprising following step:

Chiral resolution of a mixture of the enantiomers (S)-(I) and (R)-(I) of a Praziquanamine, via precipitation of a diastereomeric salt formed by one of the enantiomers (S)-(I) or (R)-(I) with an enantiopure or enantioenriched chiral 2-aryl-propionic acid containing at least 14 C-atoms.

The chiral resolution of a mixture of the enantiomers (S)-(I) and (R)-(I) of the well-known Praziquantel precursor Praziquanamine ([4-oxo-1,2,3,6,7,1-Ib-hexahydro-4H-pyrazino[2,I-a]isoquinoline]) (I) according to the invention provides a simple and efficient procedure which can be integrated in existing processes for racemic Praziquantel. This allows the preparation of (R)-Praziquantel by an appropriate adaption of existing processes for racemic Praziquantel. These existing processes (e.g. the Shin-Poong process or the original Merck process) are well established and highly optimized even on large scale. The enantiopure or enantiomerically enriched (R)-Praziquanamine obtained by the method according to the invention can be used to obtain enantiopure or enantiomerically enriched (R)-Praziquantel in large quantities.

The object of the invention has also been solved by a method for the production of enantiopure or enantiomerically enriched N-substituted [(1R)-1,2,3,4,tetrahydro-1-isoquinolin-1-yl]methanamine (N-substituted (R)-Praziquandiamine), comprising following step:

Chiral resolution of a mixture of the enantiomers (S)-(II) and (R)-(II) of N-substituted Praziquandiamine (S)-(II)

(R)-(II)

via precipitation of a diastereomeric salt formed by one of the enantiomers (S)-(II) or (R)-(II) with an enantiopure or enantioenriched 2-aryl-propionic acid containing at least 14 C-atoms, wherein $R^2$ denotes tert.-butyloxycarbonyl, benzoyl, cyclohexanoyl or acetyl, preferably acetyl (—(C═O)—CH$_3$).

In accordance with the chemical structures shown above, in the context of the present invention the term "(R)-Praziquandiamine)" refers to 1,2,3,4,tetrahydro-1-isoquinolin-1-yl]methanamine and the term "N-substituted (R)-Praziquandiamine)" refers to derivatives of 1,2,3,4,tetrahydro-1-isoquinolin-1-yl]methanamine, which carry a substituent $R^2$ at the exocyclic nitrogen atom.

Praziquandiamine is also a known precursor for the synthesis of Praziquantel. Thus, in accordance to what is described above for Praziquanamine, the method for the production of enantiopure or enantiomerically enriched N-substituted (R)-Praziquandiamine also provides a simple and efficient procedure which can be implemented in one of the well established and highly optimized large-scale processes for the synthesis of racemic Praziquantel. After all, the enantiopure or enantiomerically enriched N-substituted (R)-Praziquandiamine obtained by the method according to the invention can be used to obtain enantiopure or enantiomerically enriched (R)-Praziquantel in large quantities.

For the purpose of the present invention the term "mixture of the enantiomers" includes racemic mixtures wherein the enantiomeric ratio is 50:50 as well as enantioenriched (enantiomerically enriched) mixtures. The term "enantiopure" (enantiomerically pure) means that one enantiomer is present in an optical purity of >95% ee, preferably >98% ee. Thus, the term "enantioenriched" (enantiomerically enriched) refers here to a mixture of the two enantiomers, wherein the enantiomeric ratio is larger than 50:50 but less than 97.5:2.5.

According to the invention, the enantiopure or enantioenriched chiral 2-aryl-propionic acid contains at least 14 C-atoms, preferably between 14 and 20 C-atoms and even more preferably between 14 and 16 C-atoms. For the purpose of the present invention "aryl" refers to a residue comprising at least one aromatic hydrocarbon system having 6, 7, 8, 9 or 10 carbon atoms forming the core structure of the system. Thus, "aryl" includes monocyclic residues comprising 6 carbon atoms forming the core structure, i.e. a phenyl moiety as well as bicyclic residues comprising 10 carbon atoms forming the core structure, e.g. a naphthyl or azulenyl moiety. The monocyclic or bicyclic residues are unsubstituted or substituted with further substituents such as in particular methyl, methoxy, F, Cl, CF$_3$, benzoyl or the like. Thus, 2-(6-methoxy-naphthalen-2-yl)-propionic acid or 2-(3-benzoylphenyl)propionic acid are specific examples of enantiopure, chiral 2-aryl-propionic acids containing at least 14 C-atoms atoms. (S)-2-(6-methoxy-naphthalen-2-yl)-propionic acid, which is the API (active pharmaceutical ingredient) Naproxen, will be referred to as (S)-Naproxen, whereas its enantiomer (R)-2-(6-methoxy-naphthalen-2-yl)-propionic acid will be referred to as (R)-Naproxen. Accordingly, the (S)-enantiomer of 2-(3-benzoylphenyl)propionic acid will be referred to as (S)-Ketoprofen, whereas its corresponding (R)-enantiomer acid will be referred to as (R)-Ketoprofen.

The precipitation of the diastereomeric salt (formed by the use of either Praziquantel precursor Praziquanamine or N-substituted Praziquantel precursor Praziquandiamine) from an appropriate solvent or a solvent mixture can be performed at different temperatures. Cooling might be used to facilitate the salt formation. In this regard, appropriate solvents or solvent mixtures are hydroxylic solvents like alcohols and water or polar non-hydroxylic solvents like acetonitrile, acetone, ethyl acetate and mixtures thereof. In very specific embodiments mixtures from 2-propanol and water are used.

Subsequent to its precipitation the diastereomeric salt is separated and the enantiopure or enantiomerically enriched (R)-Praziquantel precursor ((R)-Praziquanamine or N-substituted (R)-Praziquandiamine is isolated. Thus, an important embodiment of the present invention includes a method, which further comprises following steps:

Separation of the diastereomeric salt;
Isolation of (R)-Praziquanamine.

Yet, another important embodiment includes a method, which further comprises following steps:

Separation of the diastereomeric salt;
Isolation of N-substituted (R)-Praziquandiamine (preferably (R)-Praziquanacetamide).

According to the invention, the precipitated diastereomeric salt is preferably separated via simple liquid/solid separation.

For the subsequent isolation of the (R)-Praziquantel precursor ((R)-Praziquanamine or N-substituted (R)-Praziquandiamine such as in particular (R)-Praziquanacetamide) state of the art procedures to separate the two components of an organic ammonium salt can be used, such as in particular methods which involve the treatment of the salt with aqueous alkali base in the presence of an organic solvent. In this case the organic amine is extracted into the organic phase while the organic acid is kept in the aqueous phase as alkali salt. In other embodiments the diastereomeric salt derived from either (R)-Praziquanamine or the N-substituted (R)-Praziquandiamine such as in particular (R)-Praziquanacetamide is treated with aqueous mineral acid and the organic acid is extracted by an organic solvent, while the organic ammonium mineral acid salt is kept in aqueous solution. The organic amine derived from the (R)-Praziquantel precursor can be isolated from the aqueous solution by treatment with an aqueous alkali solution and subsequent extraction of the organic amine into an organic phase. In case (R)-Praziquanamine is used as a (R)-Praziquantel precursor another possibility is to transform the organic amine from its aqueous ammonium salt solution directly (without prior isolation) to the corresponding cyclohexyl carboxamide using a two phase system (aqueous/organic), which is formed by the addition of solvent like dichloromethane, toluene, methyl-THF, THF and others. The pH-value is adjusted to above pH 8 by an aqueous base like NaOH, KOH or others. Then the organic reagent (for example an organic acid chloride, preferably cyclohexanecarboxylic acid chloride) is added in pure form or dissolved in an organic solvent like those mentioned above while the pH is kept at above 8 by simultaneous addition of aqueous base. In case (R)-Praziquanacetamide is used, the amide group is easily cleaved to obtain (R)-Praziquanamine by treatment with aqueous HCl, which is described in the literature by Rupe and Frey in Helv. Chim. Acta (1939), 22, 673 for the racemic benzamide as well as the isolation of crude racemic 1,2,3,4,tetrahydro-1-isoquinolinemethanamine. Selective acylation of (R)-1,2,3,4,tetrahydro-1-isoquinolinemethanamine at the exocyclic nitrogen was shown by Z. Czarnocki et al (Tetrahedron Asymmetry 17 (2006)1415).

In those cases, where the water solubility of the applied enantiopure, chiral 2-aryl-propionic acid is poor it is also possible to acidify the reaction mixture containing the diastereomeric salt with aqueous acid (preferably an inorganic acid or an organic sulfonic acid or trifluoroacetic acid or a mixture of any of the foregoing) to achieve disintegration of the diastereomeric salt, whereby the (R)-Praziquanamine and (R)-N-[(1,2,3,4,tetrahydro-1-isoquinolinyl) methyl]-carboxamide (preferably (R)-Praziquanacetamide) is kept in solution as ammonium salt, while the free enantiopure, chiral 2-aryl-propionic acid precipitates and is filtered off. Thus (R)-Praziquanamine and R-N-[(1,2,3,4,tetrahydro-1-isoquinolinyl)methyl]-carboxamide (such as in particular (R)-Praziquanacetamide) can be separated from the chiral acid by liquid/solid separation. In very specific embodiments the water soluble acid, which is used to acidify the reaction mixture is selected from a group consisting of HCl, HBr, HI, $H_2SO_4$, $HNO_3$, $H_3PO_4$, methane sulfonic acid, trifluoromethane sulfonic acid, toluene sulfonic acid and mixtures thereof in all ratios.

Another specific embodiment of the invention comprises methods, wherein the 2-aryl-propionic acid used as chiral acid for the resolution of the racemic Praziquantel precursor (Praziquanamine or N-substituted Praziquandiamine) is (S)-Naproxen [(S)-2-(6-methoxy-naphthalen-2-yl)-propionic acid] or (S)-Ketoprofen. The use of these chiral acids is particularly advantageous, because both are API's, which are easily available in large quantities and high purities.

In addition to this, it has been shown that (S)-Naproxen is easily separable from the Praziquantel precursors applied according to the present invention (that is (R)- or (S)-Praziquanamine as well as N-substituted (R)- or (S)-Praziquandiamine), which is very important for a straightforward and efficient recycling of the compound. Thus, a very important embodiment of the invention comprises methods, wherein the 2-aryl-propionic acid is (S)-Naproxen and the precipitated diastereomeric salt comprises (S)-Naproxen and (R)-Praziquanamine (R)-(I). In specific embodiments this salt has a stoichiometry of X:1, wherein X is a real number between 1 and 3. In particular important embodiments, the diastereomeric salt is characterized by a stoichiometry of 2:1 [(S)-Naproxen:(R)-Praziquanamine] as shown below:

The [(S)-Naproxen:(R)-Praziquanamine] 2:1 salt can be separated in high yield and high selectivity from the (S)-Praziquanamine in the mother liquor, by a simple liquid/solid separation, because it precipitates from an appropriate solvent or solvent mixture on cooling. Accordingly, the precipitation can be performed in the same reaction step as the salt formation). Appropriate solvents or solvent mixtures are hydroxylic solvents like alcohols and water or polar non-hydroxylic solvents like acetonitrile, acetone, ethyl acetate and mixtures of any of the foregoing. In specific embodiments mixtures from 2-propanol and water are used.

Of course the separation process described above has a mirror image, when (R)-Naproxen is used. Then the 2:1 salt [(R)-Naproxen:(S)-Praziquanamine] precipitates and (R)-Praziquanamine is kept in solution for further processing to (R)-Praziquantel. This specific mirror process is of course another aspect of the present invention. A further aspect could be the separation of racemic Naproxen by R-Praziquanamine. However, due to quality and feasibility considerations in preferred embodiments (R)-Praziquanamine from the [(S)-Naproxen:(R)-Praziquanamine] 2:1 salt is further processed to (R)-Praziquantel.

In a particular preferred embodiment the separation of the [(S)-Naproxen:(R)-Praziquanamine] 2:1 salt is performed via precipitation of the salt from a solvent mixture containing 2-propanol and water (preferably in a ratio between 10:1 and 1:10, and more preferably in a ratio of 4:1 or 3:2. The precipitated solid (diastereomeric salt) is filtered off (optional washing of the filter cake, preferably with cooled 2-propanol or a cooled mixture of 2-propanol/water e.g. in a ratio of 4:1 or 3:2). The (S)-enantiomer (S)-(I) remains in the mother liquor. The [(S)-Naproxen:(R)-Praziquanamine] 2:1 salt obtained after precipitation may directly be used or it may be dried prior to further processing.

A further embodiment of the invention comprises a method, wherein the 2-aryl-propionic acid is (S)-Naproxen, the N-substituted Praziquandiamine (R)-(II) is (R)-Praziquanacetamide ((R)-N[(1,2,3,4,tetrahydro-1-isoquinolinyl) methyl]-acetamide) and the precipitated diastereomeric salt comprises (S)-Naproxen and (R)-Praziquanacetamide. In specific embodiments this salt has a stoichiometry of X:1, wherein X is a real number between 1 and 3. In particular important embodiments, the diastereomeric salt is characterized by a stoichiometry of 1:1 [(S)-Naproxen:(R)-Praziquanacetamide] as shown below:

In another embodiment the 2-aryl-propionic acid is (S)-Ketoprofen, the N-substituted Praziquandiamine according to formula (R)-(II) is (R)-Praziquanacetamide and the precipitated diastereomeric salt comprises (S)-Ketoprofen and (R)-Praziquanacetamide. In a specific embodiment of the invention this salt has a stoichiometry of X:1, wherein X is a real number between 1 and 3. In particular important embodiments, the diastereomeric salt is characterized by a stoichiometry of 1:1 [(S)-Ketoprofen:(R)-Praziquanacetamide] as shown below:

The [(S)-Naproxen:(R)-Praziquanacetamide] salt as well as the [(S)-Ketoprofen:(R)-Praziquanacetamide] can be separated in high yield and high selectivity from the (S)-Praziquanacetamide in the mother liquor, by a simple liquid/solid separation, because it precipitates from an appropriate solvent or solvent mixture on cooling. Accordingly, the precipitation can be performed in the same reaction step as the salt formation). Appropriate solvents or solvent mixtures are hydroxylic solvents like alcohols and water or polar non-hydroxylic solvents like acetonitrile, acetone, ethyl acetate and mixtures thereof. Preferred are mixtures from 2-propanol and water.

Of course the separation process described above also has a mirror image, when (R)-Naproxen or (R)-Ketoprofen are used. Then the diastereomeric salt ([(R)-Naproxen:(S)-Praziquanacetamide] and [(S)-Ketoprofen:(R)-Praziquanacetamide] respectively) precipitates and (R)-Praziquanacetamide is kept in solution for further processing to (R)-Praziquantel. This specific mirror process is another aspect of the present invention. Nevertheless, due to quality and feasibility considerations in preferred embodiments (R)-Praziquanacetamide derived from the corresponding [(S)-Naproxen:(R)-Praziquanacetamide] 1:1 salt or the corresponding [(S)-Naproxen:(R)-Praziquanacetamide] 1:1 salt is further processed to (R)-Praziquantel.

The subsequent isolation of the (R)-Praziquantel precursor ((R)-Praziquanamine or N-substituted (R)-Praziquanacetamide) from the salt can be achieved by treatment of the diastereomeric salt with aqueous alkali base in the presence of an organic solvent. In this case the organic amine is extracted into the organic phase while the organic acid is kept in the aqueous phase as alkali salt. This procedure is applicable for the isolation of the (R)-Praziquantel precursor (e.g. (R)-Praziquanamine), though the extraction of the (R)-Praziquantel precursor (e.g. (R)-Praziquanamine) into an organic phase (like dichloromethane) is tedious and accompanied by loss of yield.

The free acid of (S)-Naproxen is almost insoluble in water. This property can be used for isolation of the (R)-Praziquantel precursor ((R)-Praziquanamine or (R)-Praziquanacetamide). Accordingly, very important embodiment comprises methods, wherein the diastereomeric salt is the [(S)-Naproxen:(R)-Praziquanamine] 2:1 salt and wherein the isolation of (R)-Praziquanamine from the [(S)-Naproxen:(R)-Praziquanamine] 2:1 salt is accomplished by suspension of the salt in water and subsequent addition of a water soluble acid. In such cases, the water soluble acid is preferably an inorganic acid or an organic sulfonic acid or trifluoroacetic acid or a mixture of any of the foregoing. At approximately pH 1 the salt disintegrates and (R)-Praziquanamine is kept in solution as ammonium salt, while the free acid of (S)-Naproxen precipitates and is filtered off. Due to the very low solubility of the free (S)-Naproxen this process may be performed at different temperatures such as in particular room temperature. The described process allows recycling of (S)-Naproxen in high purity with very good yields without any further purification. Accordingly, the method according to the invention provides a very efficient process to recycle and reuse (S)-Naproxen. This concept is applicable to salts consisting of (S)-Naproxen and (R)-Praziquanacetamide and the corresponding embodiment is another aspect of the present invention.

Accordingly, a specific method according to the invention comprises following steps:
  Separation of [(S)-Naproxen:(R)-Praziquanamine] 2:1 salt via liquid/solid separation;
  Isolation of (R)-Praziquanamine from the [(S)-Naproxen:(R)-Praziquanamine] 2:1 salt via acidification of the reaction mixture and (subsequent) liquid/solid separation.

And another specific method according to the invention comprises following steps:
  Separation of [(S)-Naproxen:(R)-Praziquanacetamide:] 1:1 salt via liquid/solid separation;
  Isolation of (R)-Praziquanacetamide from the [(S)-Naproxen:(R)-Praziquanacetamide] 1:1 salt via acidification of the reaction mixture and (subsequent) liquid/solid separation.

A further specific method according to the present invention comprises following steps:
  Separation of [(S)-Ketoprofen:(R)-Praziquanacetamide:] 1:1 salt via liquid/solid separation;
  Isolation of (R)-Praziquanacetamide from the [(S)-Ketoprofen:(R)-Praziquanacetamide] 1:1 salt via acidification of the reaction mixture and (subsequent) liquid/solid separation.

As described above, in particular important embodiments an inorganic acid or an organic sulfonic acid or trifluoroacetic acid is used for the acidification and in very specific embodiments this water soluble acid is selected from a group consisting of HCl, HBr, HI, $H_2SO_4$, $HNO_3$, $H_3PO_4$, methane sulfonic acid, trifluoromethane sulfonic acid, toluene sulfonic acid and mixtures thereof.

After all, a particular important embodiment of the present invention comprises a method, wherein
the 2-aryl-propionic acid is (S)-Naproxen and the precipitated diastereomeric salt comprises (S)-Naproxen and (R)-Praziquanamine (R)-(I);
the diastereomeric salt is [(S)-Naproxen:(R)-Praziquanamine], which has a stoichiometry of X:1, wherein X is a real number between 1 and 3;
the method further comprises following steps:
Separation of the diastereomeric salt [(S)-Naproxen:(R)-Praziquanamine] via liquid/solid separation;
Isolation of (R)-Praziquanamine via acidification of the reaction mixture and (subsequent) liquid/solid separation.

Analogously another particular important embodiment of the present invention comprises a method, wherein
the 2-aryl-propionic acid is (S)-Naproxen or (S)-Ketoprofen, the N-substituted (R)-Praziquandiamine according to formula (R)-(II) is (R)-Praziquanacetamide;
the diastereomeric salt has a stoichiometry of X:1, wherein X is a real number between 1 and 3;
the method further comprises following steps:
Separation of the diastereomeric salt via liquid/solid separation;
Isolation of (R)-Praziquanacetamide (as aqueous ammonium salt solution) via acidification of the reaction mixture and (subsequent) liquid/solid separation.

The isolated (R)-Praziquanamine can be converted to (R)-Praziquantel via N-acylation using a reactive derivative of cyclohexanecarboxylic acid.

Thus, another aspect of the invention comprises methods, which combine the method for the production of (R)-Praziquanamine as described above with following step:
Reaction of the (R)-Praziquanamine with a cyclohexanecarboxylic acid derivative.

In a particular straightforward embodiment the aqueous filtrate obtained after the precipitation of (S)-Naproxen is directly—or after concentration in vacuum-applied for the N-acylation reaction without prior work-up procedures such as extraction and/or (partial) solvent evaporation. This is particular advantageous in case the N-acylation reaction is performed in a biphasic solvent system, wherein one solvent is water (preferably under Schotten-Baumann conditions). In such cases the aqueous filtrate is preferably mixed with an organic solvent (e.g. dichloromethane) to form a biphasic system and the pH is adjusted to 5.6 or above using an appropriate base (for example an aqueous solution of NaOH) prior to the addition of the reactive cyclohexylcarboxylic acid derivative. All subsequent steps of the N-acylation reaction can be performed according to known procedures.

In a particular preferred embodiment of the present invention the reactive cyclohexanecarboxylic acid derivative used in the N-acylation reaction is cyclohexanecarboxylic acid chloride, but the reaction can also be performed using other reactive derivatives like mixed anhydrides or appropriate amide bond formation methods, which are known from peptide bond formation and described in literature (e.g. Madeleine M. Joullié and Kenneth M. Lassen ARKIVOC 2010 (viii) 189-250).

In embodiments were the Praziquantel precursor is an N-substituted (R)-Praziquandiamine, wherein $R^2$ denotes tert. Butyloxycarbonyl, benzoyl or acetyl, the isolated N-protected (R)-Praziquandiamine can for example be converted to (R)-Praziquantel via following reaction sequence, wherein the different reaction steps can be performed e.g. in analogy to the procedures described by Rupe and Frey in Hey. Chim. Acta 1939, 22, 673 and Z. Carnocky et al Tetrahedron Asymmetry 17 (2006)1415:

Thus, another embodiment of the present invention includes a method for the production of enantiopure or enantiomerically enriched (R)-Praziquantel comprising a method as described above and following steps:

Deprotection of the N-substituted (R)-Praziquandiamine (R)-(II);

Reaction of unprotected (R)-Praziquandiamine obtained in a) with a reactive cyclohexylcarboxylic acid derivative;

Cyclisation of the carboxamide obtained in b) with chloroacetyl chloride.

In a very particular embodiment the substituent R² of the N-substituted (R)-Praziquandiamine (R)-(II) is an acetyl group. In this specific case the reaction sequence is as follows (again, the steps can be performed e.g. in analogy to the procedures described by Rupe and Frey in Hev. Chim. Acta 1939, 22, 673 and Z. Carnocky et al Tetrahedron Asymmetry 17 (2006)1415):

production process according to the invention or several times in a row. The recycling of the unwanted (S)-Praziquanamine reduces waste and thus significantly improves the overall efficiency. The method according to the invention provides a simple and efficient process for the preparation of enantiopure or enantiomerically enriched (R)-Praziquanamine and thus for (R)-Praziquantel, which can be integrated into the already existing and well established racemic production processes to enhance their efficiency.

The method according to the invention includes processes where the starting material is racemized completely or partially. A partial racemization might be useful to keep side reactions low and such a procedure may still be efficiently used e.g. in cyclic procedures, where the racemization/chiral resolution sequence is performed several times in a row.

According to the invention derivatives of (S)-Praziquanamine include in particular nitrogen-protected derivatives according to formula (S)-(I)-PG:

In embodiments were R is cyclohexanoyl, there is no need to perform a deprotection step and the cyclisation of the carboxamide can be performed immediately after the isolation of the Praziquandiamine derivative.

Another important embodiment of the invention comprises methods for the production of enantiopure or enantiomerically enriched (R)-Praziquantel, which further comprise following step:

Racemization of (S)-Praziquanamine or derivatives thereof

The (S)-Praziquanamine can be obtained from the mother liquor after precipitation and separation of the diastereomeric salt. The combination of the chiral resolution with the racemization step provides a very valuable recycling procedure, which might be performed only once within the

(S)-(I)-PG wherein the protecting group PG denotes tert-butyloxycarbonyl, benzoyl or acetyl, preferably tert.-butyloxycarbonyl.

Thus, another aspect of the present invention relates to methods comprising following step:

Racemization of enantiomerically pure or enantiomerically enriched compound according formula (I')

(I')

wherein
a base is used, and
R¹ denotes H, tert.-butyloxycarbonyl, benzoyl or acetyl, preferably H, or tert.-butyloxycarbonyl.

Again, this method according to the invention includes processes where the starting material is racemized completely or partially. A partial racemization might be useful to keep side reactions low and such a procedure may still be efficiently used e.g. in cyclic procedures, where the racemization/chiral resolution sequence is performed several times in a row. In a process for the production of (R)-Praziquantel the racemization procedure can be used to recycle the (S)-enantiomer (S)-(I') obtained after the chiral resolution in order to enhance the overall efficiency.

Much to our surprise we found, that enantiopure (R)- or (S)-Praziquanamine as well as enantiopure N-protected Praziquanamine like (S)-(I)-PG racemizes, by treatment with appropriate bases under appropriate conditions.

Different bases might be used to achieve appropriate basic conditions for the racemization of the enantiomerically pure or enantiomerically enriched Praziquantel precursor according to formula (I'). However, it has been shown that a proper selection of the base is an important factor in view of possible side reactions, which usually lead to decomposition of the starting material.

A very important embodiment of the present invention comprises methods, wherein the base used for the racemization of the Praziquantel precursor according to formula (I') is a tertiary alkali alkoxide. Tertiary alkali alkoxides such as alkali tert.-butoxides or alkali tert.-pentoxides as well as their higher homologues are easily available standard reagents, but most of all, they allow to perform the racemization reaction with very good yield with a low level of unwanted decomposition reactions. In a particular advantageous embodiment of the invention sodium or preferably potassium tert.-butoxide is used for the racemization. This reagent allows performing the racemization with remarkably high yield within a very short reaction time.

In another specific embodiment of the present invention, the racemization of the Praziquantel precursor according to formula (I') is performed in a dipolar aprotic reaction medium. In specific embodiments the dipolar aprotic reaction medium is selected from a group consisting of N-Methyl-2-pyrrolidone, dimethylformamide, dimethylsulfoxide, tetrahydrofuran, methyltetrahydrofuran (MethylTHF), dioxane and mixtures thereof in all ratios, preferably the reaction medium is tetrahydrofuran. Suitable mixtures include for example mixtures of tetrahydrofuran and dimethylsulfoxide (in particular tetrahydrofuran in combination with 0.3 eq to 1.0 eq of dimethylsulfoxide), which might be useful to accelerate the racemization reaction. However, most preferably the dipolar aprotic medium is tetrahydrofuran alone. It was noted that unwanted side reactions can be reduced if the reaction mixture contains only little or no water.

Other parameters that influence the racemization reaction are the base stoichiometry and the temperature. Important embodiments of the invention comprise methods, wherein the amount of base used in the racemization process is in the range between 0.05 eq to 1.5 eq, preferably 0.3 eq to 1.0 eq and most preferably 0.4 eq to 0.8 eq. Furthermore the racemization of the Praziquantel precursor according to formula (I') is preferably performed a temperature in the range between −50° C. and +40° C., preferably between −25° C. and +30° C., and—in particular in case R¹ is H—the temperature is most preferably between 0° C. and 30° C.

After all, a very specific embodiment of the invention refers to a method for the racemization of enantiomerically pure or enantiomerically enriched compounds according formula (I') using basic conditions (I')

wherein
R¹ denotes H, tert.-butyloxycarbonyl, benzoyl or acetyl, preferably H, or tert.-butyloxycarbonyl;
the base is a tertiary alkali alkoxide, preferably sodium or potassium tert.-butoxide and even more preferably potassium tert.-butoxide;
the dipolar aprotic reaction medium is selected from a group consisting of N-Methyl-2-pyrrolidone, dimethylformamide, dimethylsulfoxide, tetrahydrofuran, methyltetrahydrofuran, dioxane and mixtures thereof in all ratios, preferably the reaction medium is tetrahydrofuran;
the amount of base used in for the racemization is in the range between 0.05 eq to 1.5 eq, preferably 0.3 eq to 1.0 eq and most preferably 0.4 eq to 0.8 eq;
the racemization is performed at a temperature in the range between −50° C. and +40° C., preferably between −25° C. and +30° C., and—in particular in embodiments were R¹ is H—most preferably between 0° C. and 30° C.

In this specific embodiment the enantiomer used in the racemization might particularly be the (S)-Praziquanamine. As indicated above, side reactions might be reduced if the reaction mixture contains only little or no water. It is preferred to utilize this specific racemization process to improve processes for the preparation of enantiopure or enantiomerically enriched (R)-Praziquantel based on chiral resolution of racemic Praziquanamine by transferring enantiopure or enantiomerically enriched (S)-Praziquanamine into its racemate (or close to the racemic composition), which is then submitted to a chiral resolution.

A further aspect of the invention relates to a salt consisting of the (R)-Praziquanamine and (S)-Naproxen or solvates thereof. This salt is preferably characterized by a stoichiometry of X:1 ((S)-Naproxen:(R)-Praziquanamine), where X is any real number between 1 and 3 but preferably X is 2 as shown below:

Another aspect of the present invention relates to the use of a salt consisting of (R)-Praziquanamine and (S)-Naproxen with a preferred stoichiometry of 2:1 ((S)-Naproxen:(R)-Praziquanamine) or solvates thereof in a method according to the invention as described above.

Another aspect of the invention relates to a salt consisting of (R)-Praziquanacetamide derivative and (S)-Naproxen or (S)-Ketoprofen and solvates thereof. These salts are preferably characterized by a stoichiometry of X:, wherein X is a real number between 1 and, 3 but preferably X is 1 as e.g. shown below (a) (S)-Naproxen salt and b) (S)-Ketoprofen salt):

Another aspect of the present invention relates to the use of a salt consisting of (R)-Praziquanacetamide and (S)-Naproxen or (R)-Praziquanacetamide and (S)-Ketoprofen or solvates of any of the foregoing in a method according to the invention as described above.

The term "solvates" means addition forms of the compounds of the present invention with solvents, preferably pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or multihydrate. If the solvent is alcohol, the solvate formed is an alcoholate, e.g., a methanolate or ethanolate. If the solvent is an ether, the solvate formed is an etherate, e.g., diethyl etherate.

The compounds of the present invention can be prepared according to the procedures of the following Schemes and Examples, using appropriate materials and are further exemplified by the following specific examples.

The invention will be illustrated, but not limited, by reference to the specific embodiments described in the following examples. Unless otherwise indicated in the schemes, the variables have the same meaning as described above.

The starting materials for the preparation of compounds of the present invention can be prepared by methods as described in the examples or by methods known per se, as described in the literature of synthetic organic chemistry and known to the skilled artisan, or can be obtained commercially.

Unless otherwise specified, all starting materials except the Praziquantel precursors such as e.g. rac-Praziquanamine are obtained from commercial suppliers and used without further purifications. The Praziquantel precursors (e.g. Praziquanamine and Praziquandiamine) are intermediates in known procedures for the synthesis of Praziquantel such as in particular the original Merck process as well as in the Shin-Poong process for rac-Praziquantel. Unless otherwise specified, all temperatures are expressed in ° C. and all reactions are conducted at RT.

EXPERIMENTAL SECTION

Abbreviations

Abbreviations:
ee enantiomeric access
rac racemic
HPLC High Performance Liquid Chromatography
J Coupling constant
KOtBu potassium tert.-butoxide
m Multiplet
mL Milliliter
mp Melting Point
MS Mass Spectrometry
(S)-PZQ (S)-Praziquantel
(R)-PZQ (R)-Praziquantel
RT Room Temperature
s Singulet
t Triplet
THF Tetrahydrofuran Example 1

Preparation of (R)-Praziquanamine on the Basis of Racemic Praziquanamine Utilizing a Cyclic Process

1.1: Chiral Resolution of Racemic Praziquanamine by Formation of (R)-Praziquanammonium (S)-2-(6-Methoxy-naphthalen-2-yl)-propionate Salt (Stoichiometry 1:2)

520 g (2.54 mol) racemic Praziquanamine (HPLC-purity 98,8%) and 585 g (2.54 mol) (S)-Naproxen are heated under stirring in a solvent mixture made from 2-propanol (4010 g) and deionized water (1005 g) up to 65° C. until complete dissolution. The resulting solution is stirred and cooled down to −19° C. while salt precipitation starts at about 45° C. When the target temperature is met, the precipitate is filtered off, the filter cake is washed once with 780 g of a cooled (−20° C.) solvent mixture from 2-propanol and water (4/1) and then twice each time with 780 g of cooled (−20° C.) 2-propanol. After drying (24 h at 50° C. under vacuum) 746.7 g (1.13 mol) of R-Praziquanamine/Naproxen salt (R/SS) are obtained as a white solid (88.7% of theory) with an enantiomeric excess related to (R)-Praziquanamine of 98.6%.

After evaporation of the mother liquor and washing portions a yellow residue of 351.1 g is isolated containing residual (S)-Naproxen and (S)-Praziquanamine with an enantiomeric excess related to (S)-Praziquanamine of 70.2%.

$C_{40}H_{42}O_7N_2$ (662.77 g.mol−1), mp. 157-159° C.

$^1$H NMR(CD$_3$OD): 6.14-6.19 (m, 6Harom), 5.87 (dt, J=8, 2 Hz, 2Harom), 5.62-5.72 (m, 6Harom), 5.56 (ddd, J=8, 4, 2 Hz, 2Harom), 3.31 (dd, J=8, 4 Hz, 1H), 3.14-3.18 (m, 1H), 2.35 (s, 6H), 2.28 (dd, J=12, 8 Hz, 2H), 2.23 (dd, J=8, 4 Hz, 1H), 1.98 (AB, J=18 Hz, 2H), 1.77-1.79 (m, 4H), 1.21-1.38 (m, 4H), 0.01 (d, J=8 Hz, 6H).

$^{13}$C NMR(CD$_3$OD): 177.2 (s, 2CO$_2$H), 167.5 (s, 1C=0), 157.6 (s, 2COMe), 136.2 (s, 2qC$_{arom}$), 134.5 (s, 1qC$_{arom}$), 133.7 (s, 2qC$_{arom}$), 133.6 (s, 1qC$_{arom}$), 129.0 (s, 2qC$_{arom}$), 128.8 (s, 1C$_{arom}$), 128.7 (s, 2C$_{arom}$), 126.7 (s, 1C$_{arom}$), 126.6 (5, 2C$_{arom}$), 126.4 (s, 1 C$_{arom}$), 125.8 (s, 2C$_{arom}$), 125.4 (s, 2C$_{arom}$), 124.5 (s, 1C$_{arom}$), 118.4 (s, 2C$_{arom}$), 105.2 (s, 2C$_{arom}$), 55.7 (s, 1CH), 54.3 (s, 2OCH$_3$), 48.3 (s, 1CH$_2$), 48.1 (s, 1CH$_2$), 45.3 (s, 2CH), 38.8 (s, 1CH$_2$), 28.2 (s, 1CH$_2$), 17.6 (s, 2CH$_3$).

Figure 1:
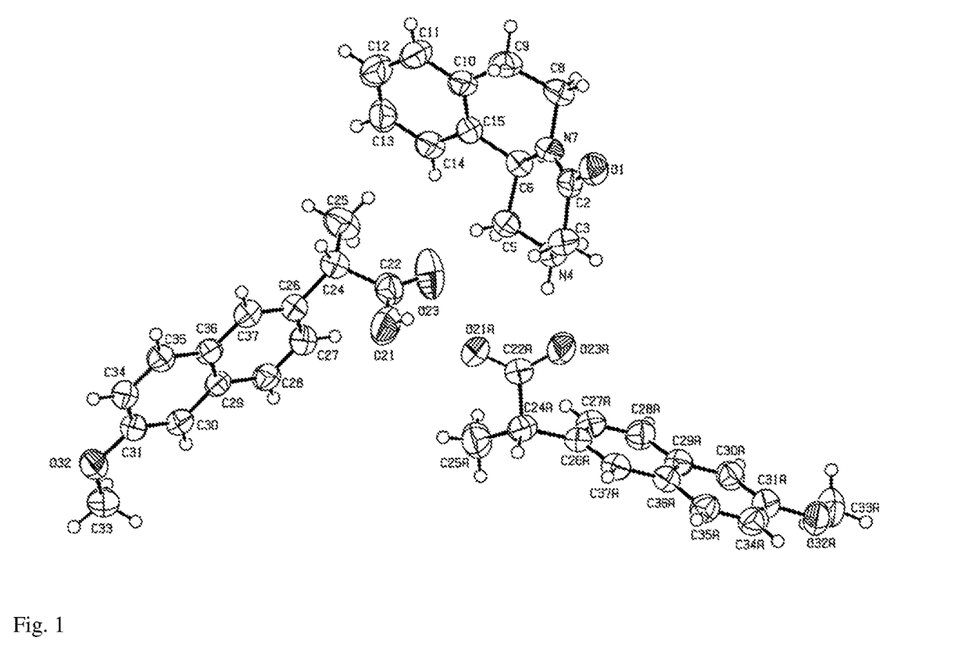
FIG. 1. Concerns XRD-analysis: Diffractometer/Detector: SuperNova (Agilent), Atlas CCD Detector; radiation: Cu Kα (1.5418 Å), X-ray mirrors; temperature 200 K; crystal system orthorhombic; Space group: P2$_1$2$_1$2$_1$; Lattice parameters: a, b, c: 5.98347(19) Å, 22.2133(8) Å, 25.4991(9) Å; α, β, γ: 90.00°, 90.00°, 90.00°.

XRD-analysis: Diffractometer/Detector: SuperNova (Agilent), Atlas CCD Detector; radiation: Cu Kα (1.5418 Å), X-ray mirrors; temperature 200 K; crystal system ortho-rhombic; Space group: P2$_1$2$_1$2$_1$; Lattice parameters: a, b, c: 5.98347(19) Å, 22.2133(8) Å, 25.4991(9) Å; α, β, γ: 90.00°, 90.00°, 90.00°. See FIG. 1.

1.2: Release of (R)-Praziquanamine, Precipitation of (S)-Naproxen and conversion of (R)-Praziquanamine to (R)-Praziquantel 300 g (0.453 mol) of (R)-Praziquanamine/(S)-Naproxen salt obtainable according to 1.1 are suspended under stirring in 1200 g deionized water. 145.2 g (1 mol) aqueous hydrochloric acid (25%-w) are added dropwise at 20° C. The pH of the mixture drops to about 1 while stirring of the suspension gets easier. After complete addition, the mixture is stirred for further 30 min before filtration. The filter cake is then washed three times each time with 200 g deionized water. After drying (24 h at 50° C. under vacuum) 204.8 g (0.890 mol) of Naproxen are isolated as a white solid (97.9% of theory) and can be reused for resolution of (R)-Praziquanamine.

The aqueous filtrate and washing portions are gathered and dichloromethane (1330 g) is added. While stirring 113.2 g (0.906 mol) aqueous NaOH (32%-w) are added at room temperature, while the pH rises to about 5.6. Cyclohexanecarboxylic acid chloride (69.60 g, 0,475 mol) is consequently added dropwise within 30 minutes, while keeping the pH in the range between 7,5 and 11,5 by parallel addition of 56.3 g (0.453 mol) aqueous NaOH (32%-w). After complete addition 20 g (0.16 mol) additional aqueous NaOH (32%-w) are added reaching a pH of 13 and the biphasic mixture is stirred for further 90min. Agitation is finally stopped and the phases are allowed to settle. The organic phase is separated and the aqueous phase is extracted twice each with 332.5 g dichloromethane. The combined organic phases are repeatedly and thoroughly washed with deionized water and evaporated. The residue is taken up in a mixture of ethanol (129 g) and n-heptane (300 g) and dissolved under stirring at 55° C. The resulting solution is cooled down to −35° C. and stirred for 30 min at −35° C. before filtration. The filter cake is washed three times each time with 143 g of a cold (−25° C.) mixture made from n-heptane/ethanol (7/3 w/w). After drying (16 h at 40° C. under vacuum) 122.9 g (0.391 mol) of (R)-Praziquantel are isolated as a white solid (86% of theory) with a HPLC-purity of 99.6% and an enantiomeric excess of 99.8% (R).

$C_{19}H_{24}N_2O_2$ (312.42 g.mol−1), mp. 109-110° C.

1.3: Racemization of (S)-Praziquanamine from the Mother Liquor of Resolution The light brown residue (351.1 g) from the mother liquor and washings of rac-Praziquanamine resolution obtainable according to 1.1 is suspended under stirring in 1400 g of deionized water. 386.4 g (2.65 mol) aqueous hydrochloric acid (25%-w) are added dropwise at 20° C. The pH of the mixture drops to about 1 while the brown solid is dissolving. After 3 h stirring there is only white suspended solid left which is filtered. The filter cake is washed with diluted aqueous HCl and dried (24 h at 40° C. under vacuum)

resulting in 60.7 g (0.264 mol) of white to light red solid characterized as (S)-Naproxen.

An aliquot of two thirds from the aqueous filtrate is taken and 99 g (2.47 mol) of solid NaOH are added under stirring and temperature control at about 25° C., the pH reaching 12-13. The hence released Praziquanamine is thoroughly extracted with dichloromethane, the combined organic layers are finally evaporated affording 167.6 g (0.829 mol) of a yellowish-orange residue of Praziquanamine with a HPLC-purity of 96.4% and an enantiomeric excess of ee=78.9% (S).

An aliquot of 40 g (0.191 mol) from this residue is dissolved under stirring in 250 g THF at 35° C. and then cooled to room temperature. Under inert atmosphere (oxygen and moisture excluded) a solution of 11 g (0.098 mol) of potassium tert.-butoxide dissolved in 140 g THF is added dropwise under temperature control. The reaction mixture immediately gets dark purple and is stirred for 6 hours at 23° C. after complete addition. 56 g (0.383 mol) aqueous HCl (25%-w) are finally added, the pH is then adjusted to 9-10 through addition of aqueous NaOH (35%-w). 600 g water and 700 g dichloromethane are added, the phases are separated and the aqueous layer is extracted thoroughly with Dichloromethane. Evaporation of the combined organic layers affords 34.9 g (0.167 mol) of an orange oily residue of racemized Praziquanamine with a HPLC-purity of 96.8% and an enantiomeric excess of 2% (S) (yield of racemization: 87.4% of theory).

1.4: Resolution of Racemized Praziquanamine by (R)-PZQ-Amine/Naproxen Salt Formation

17 g (0.084 mol) of the racemized Praziquanamine obtainable according to 1.3 and 19.35 g (0.084 mol) Naproxen are processed according to the procedure of diastereomeric salt formation as it has been described above. 21.3 g (0.0317 mol) of (R)-Praziquanamine/Naproxen salt (R/SS) are obtained as a white solid (76% of theory) with an enantiomeric excess of 99.2% (R).

Recalculation shows, that the reaction sequence described above, which includes the recycling of the false (S)-enantiomer allows an increase of the overall resolution yield up to 60% (theoretically possible overall yield being 75%) compared to a process without a recycling step.

The cyclic procedure described in this example can be easily modified in case other compounds according to formula (I') or (S)-(I)-PG shall be used in the racemization process. By way of example, in case the BOC-protected Praziquanamin (R$^1$=tert-butyloxycarbonyl) is used in the racemization, the racemic material is deprotected to yield Praziquanamine (R$^1$=H) prior to the chiral resolution. In addition the cyclic process might also be used for the synthesis of any of the Praziquantel precursors according to formula (I'), in this case a corresponding chemical conversion of enantiomerically pure or enantiomerically enriched (R)-Praziquanamine (R$^1$=H) is performed after the chiral resolution step.

Example 2

Synthesis of 4-Oxo-1,3,4,6,7,11b-hexahydro-pyrazino[2,1-a]isoquinoline-2-carboxylic acid tert-butyl ester (BOC-protected-Praziquanamine)

A solution of 10.8 g (0.049 mol) tert.-butyloxycarbonyl-tert.-butyl carbonate in ml dichloromethane is slowly added to 10 g (0.049 mol) rac-Praziquanamine (1,2,3,6,7,11b-Hexahydro-pyrazino[2,1-a]isoquinolin-4-one) dissolved in 60 ml dichloromethane at room temperature. The reaction mixture is stirred for 4 hours. After dilution with 50 ml of dichloromethane the reaction mixture is washed with 72 g (0.049 mol) of aqueous HCl (2.5%-w) and subsequently with deionized water. Evaporation of the organic layer affords 14.52 g (0.048 mol) of BOC-protected rac-Praziquanamine as a white solid with an HPLC-purity of 99.6% (98% of theory).

$C_{17}H_{22}N_2O_3$ (302.38 g.mol–1), mp. 118-121° C.

$^1$H NMR(CDCl3): 7.16-7.28 (m, $^4H_{arom}$), 4.81-4.88 (m, 2H), 4.63-4.76 (m, 1H), 4.50 (AB, J=18 Hz, 1H), 3.87 (AB, J=18 Hz, 1H), 2.74-3.03 (m, 4H), 1.51 (s, 9H).

$^{13}$C NMR(CDCl3): 165.3 (s, 1C=O), 153.8 (s, 1C=O), 135.0 (s, 1q$C_{arom}$), 132.8 (s, 1q$C_{arom}$), 129.3 (s, 1$C_{arom}$), 127.4 (s, 1 $C_{arom}$), 126.8 (s, 1$C_{arom}$), 125.3 (s, 1$C_{arom}$), 81.0 (s, 1qC), 55.3 (s, 1CH), 47.8 (s, 1CH$_2$), 46.5 (s, 1CH$_2$), 38.9 (s, 1CH$_2$), 28.8 (s, 1CH$_2$), 28.4 (s, 3CH$_3$).

The enantiomerically enriched (S)-BOC-protected-Praziquanamine can be prepared analogously starting from enriched (S)-Praziquanamine, which is for example obtainable from the mother liquor of the chiral resolution.

Example 3

Racemization of Enantiomerically Enriched (S)-BOC-protected-Praziquanamine To a solution of enantiomerically enriched (S)-Boc-protected-Praziquanamine 16.7 g (0.054 mol, HPLC-purity 97.9%, R/S=11/89) in 130 ml THF a solution of 1.5 g (0.013 mol) potassium tert.-butoxide in 14 ml of THF is slowly added under exclusion of moisture and oxygen. The dark orange mixture is stirred at room temperature for 2 hours. The reaction mixture is then poured into 100 ml of water containing 1.1 g (0.018 mol) of acetic acid. After addition of dichloromethane, phase separation and extractions with dichloromethane, the combined organic layers are evaporated affording 16.2 g (0.052 mol) of BOC-protected rac-Praziquanamine as a yellow/orange solid with a HPLC-purity of 96.7% and enantiomeric excess of 1.6%(S) (96% of theory).

The BOC-protected rac-Praziquanamine is finally deprotected to rac-Praziquanamine by standard conditions and can be reused for a new resolution step as described above.

Example 4

Preparation of (R)-Praziquantel on the Basis of Racemic Praziquanacetamide (N-((1,2,3,4-Tetrahydro-1-isoquinolinyl)methyl)-acetamide)

4.1. Preparation of Rac-Praziquanacetamide (N-((1,2,3,4-Tetrahydro-1-isoquinolinyl)methyl)-acetamide)

$^1$H NMR(CD$_3$SOCD$_3$): 7.9 (t, J=8 Hz, 1NH), 7.05-7.15 (m, 4Harom), 3.89 (dd, J=8 Hz, 4 Hz, 1H), 3.43-3.51 (m, 1H), 3.11-3.20 (m, 1H), 2.99-3.08 (m, 1H), 2.79-2.86 (m, 1H), 2.67 (t, J=8 Hz, 2H), 1.85 (s, 3H)

Preparation is performed according to the known Merck process as e.g. described in DE 25 04 250.

4.2: Chiral Resolution of Rac-Praziquanacetamide (N-((1,2,3,4-Tetrahydro-1-isoquinolinyl)methyl)-acetamide) and Isolation of (R)-Praziquanacetamide/Naproxen Salt 8 g (39.2 mmol) racemic Praziquanacetamide and 9 g (39.1 mmol) Naproxen are heated under stirring in acetonitrile (125 g) up to 80° C. until complete dissolution. The resulting solution is stirred and cooled down to 10° C. while salt precipitation occurs. When the target temperature is met, the precipitate is immediately filtered off and the filter cake washed once with 20 g of cold acetonitrile (4° C.). After drying (24 h at 40° C. under vacuum) 4.5 g (10.4 mmol) of (R)-Praziquanacetamide/Naproxen salt (R/S) are obtained as a white solid (53% of theory) with an enantiomeric excess of 97.4% (R) enantiomer.

Alternatively this salt could also be isolated for example from acetone or isopropanol/water mixtures.

It is possible to recrystallize this salt from acetonitrile in order to increase the enantiomeric excess up to 100%. It is anyway not required for the synthesis of enantiopure R-Praziquantel due to the number of following steps whereas the enantiopurity of the intermediates will be improved through purification steps.

$C_{26}H_{29}O_4N_2$ (434.53 g.mol−1), mp. 155-156° C.

$^1$H NMR(CD$_3$OD): 6.14-6.17 (m, 3H$_{arom}$), 5.93 (dd, J=8, 2 Hz, 1H$_{arom}$), 5.70-5.72 (m, $^3$H$_{arom}$), 5.63-5.65 (m, 2H$_{arom}$), 5.56 (m, 1H$_{arom}$), 2.88 (dd, J=12 Hz, 4 Hz, 1 H), 2.37 (s, 3H), 2.23 (dd, J=14, 8 Hz, 1H), 2.14-2.18 (m, 1H), 2.01-2.07 (m, 1H), 1.86-1.92 (m, 1H), 1.78-1.82 (m, 2H), 1.60-1.66 (m, 1H), 1.37-1.47 (m, 2H), 0.42 (s, 3H), 0.01 (d, J=8 Hz, 3H).

$^{13}$C NMR(CD$_3$OD): 181.4 (s, 1CO$_2$H), 173.1 (s, 1C=O), 157.4 (s, 1COMe), 138.1 (s, 1qC$_{arom}$), 133.5 (s, 1qC$_{arom}$), 132.9 (s, 1qC$_{arom}$), 131.2 (s, 1qC$_{arom}$), 129.0 (s, 1qC$_{arom}$), 128.9 (s, 1C$_{arom}$), 128.7 (s, 1C$_{arom}$), 127.4 (s, 1C$_{arom}$), 126.5 (s, 1C$_{arom}$), 126.4 (s, 1C$_{arom}$), 126.3 (5, 1C$_{arom}$), 126.2 (5, 1C$_{arom}$), 125.2 (s, 1C$_{arom}$), 118.2 (s, 1C$_{arom}$), 105.2 (s, 1C$_{arom}$), 55.1 (s, 1CH), 54.3 (s, 1OCH$_3$), 47.5 (s, 1CH), 42.5 (s, 1CH$_2$), 38.7 (s, 1CH$_2$), 26.0 (s, 1CH$_2$), 21.1 (s, 1CH$_3$), 18.1 (s, 1CH$_3$).

Figure 2:
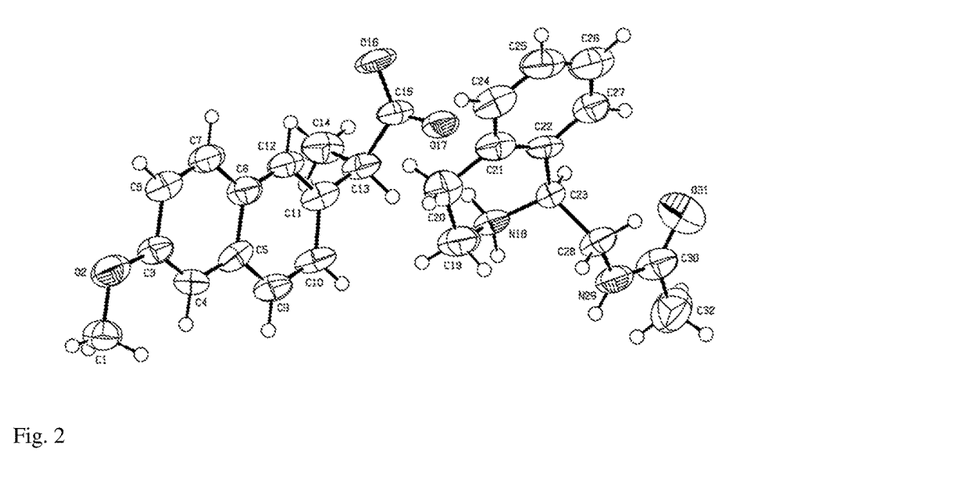
FIG. 2. Concerns XRD-analysis: Diffractometer/Detector: SuperNova (Agilent), Atlas CCD Detector; radiation: Cu Kα (1.5418 Å), X-ray mirrors; temperature 200 K; crystal system orthorhombic; Space group: P2$_1$2$_1$2$_1$; Lattice parameters: a, b, c: 6.1006(4) Å, 16.783(2) Å, 22.818(5) Å; α, β, γ: 90.00°, 90.00°, 90.00°.

XRD-analysis: Diffractometer/Detector: SuperNova (Agilent), Atlas CCD Detector; radiation: Cu Kα (1.5418 Å), X-ray mirrors; temperature 200 K; crystal system orthorhombic; Space group: P2$_1$2$_1$2$_1$; Lattice parameters: a, b, c: 6.1006(4) Å, 16.783(2) Å, 22.818(5) Å; α, β, γ: 90.00°, 90.00°, 90.00°. See FIG. 2.

4.3. Isolation of (R)-Praziquanacetamide and Preparation of (R)-Praziquantel

(R)-Praziquanacetamide is easily obtained from its salt (with Naproxen or Ketoprofen) through addition of an excess (4 eq) of acid (for example hydrochloric acid) to the salt suspension in water. After filtration of the released free chiral acid (Naproxen or Ketoprofen) and thoroughly washing of the cake with water (recovery rate of chiral acid: at least 97%), (R)-Praziquanacetamide hydrochloride salt is quantitatively released and can be converted in-situ to (R)-Praziquandiamine just by heating up to 95-100° C. for several hours. After cooling, neutralization with sodium hydroxide and extractions with methyl-THF, (R)-Praziquandiamine is directly involved in the synthesis of the corresponding carboxamide precursor according to a described procedure (J. Seubert (Merck Patent GmbH), DE2504250 (A1)).

(R)-Praziquantel is subsequently prepared from the carboxamide precursor through cyclization with chloro-acetyl chloride also according to reported procedures as e.g.:

Houben-Weyl, Vol. XI/2, Stuttgart 1958, 518-546;
J. Seubert (Merck Patent GmbH), DE 25 04 250; or
R. Pohlke, F. Loeblich, J. Seubert, H. Thomas, P. Andrews (Merck Patent GmbH), U.S. Pat. No. 3,993,760.

Example 5

(R)-Praziganacetamide/Ketoprofen Salt ((R)-N-((1,2,3,4-Tetrahydro-1-isoquinolinyl)methyl)-acetamide-(S)-2-(3-Benzoyl-phenyl-2-yl)-propionic acid Salt)

8 g (39.2 mmol) racemic (Praziquanacetamide and 9.96 g (39.2 mmol) Ketoprofen are heated under stirring in acetonitrile (340 g) up to 80° C. until complete dissolution. The resulting solution is stirred and cooled down to −20° C. When the target temperature is met, the mixture is further stirred for 2 h allowing salt precipitation. The precipitate is subsequently filtered off and the filter cake washed once with 16 g of cold acetonitrile (−20° C.). After drying (24 h at 40° C. under vacuum) 3.5 g (7.6 mmol) of (R)-Praziquanacetamide/Ketoprofen salt (RIS) are obtained as a white solid (39% of theory) with an enantiomeric excess of 93.9% (R) enantiomer.

$C_{28}H_{30}O_4N_2$ (458.55 g.mol−1), mp. 116-118° C.

$^1$H NMR(CD$_3$OD): 6.2-6.32 (m, 3Harom), 6.11-6.18 (m, 3Harom), 6.03-6.07 (m, 2Harom), 5.95-5.99 (t, J=8 Hz, 1Harom), 5.76-5.82 (m, 3Harom), 5.71-5.74 (m, 1Harom), 3.02 (dd, J=8, 4 Hz, 1H), 2.20-2.28 (m, 2H), 2.11-2.17 (m, 1H), 1.98-2.04 (m, 1H), 1.84-1.86 (m, 1H), 1.73-1.79 (m, 1H), 1.47-1.60 (m, 2H), 0.47 (s, 3H), 0.01 (d, J=8 Hz, 3H).

$^{13}$C NMR(CD$_3$OD): 197.2 (s, 1C=O), 180.0 (s, 1CO$_2$H), 173.2 (s, 1C=O), 143.8 (s, 1qCarom), 137.5 (s, 1qCarom), 137.3 (s, 1qCarom), 132.6 (s, 1qCarom), 132.3 (s, 1Carom), 131.7 (s, 1Carom), 130.6 (s, 1qCarom), 129.6 (s, 2Carom), 128.9 (s, 1Carom), 128.8 (s, 1Carom), 128.0 (s, 2Carom), 127.9 (s, 1Carom), 127.7 (s, 1Carom), 127.6 (s, 1Carom), 126.5 (s, 1Carom), 126.3 (s, 1Carom), 55.1 (s, 1CH), 50.3 (s, 1CH), 42.3 (s, 1CH$_2$), 38.7 (s, 1CH$_2$), 25.7 (s, 1CH$_2$), 21.1 (s, 1CH3), 18.2 (s, 1CH$_3$)

Alternatively this salt could also be isolated for example from ethyl acetate.

It is possible to recrystallize this salt from acetonitrile in order to increase the enantiomeric excess up to 100%. It is anyway not required for the synthesis of enantiopure (R)-Praziquantel due to the number of following steps whereas the enantiopurity of the intermediates will be improved through purification steps.

The invention claimed is:
1. A method for preparing enantiopure or enantiomerically enriched (R)-Praziquanamine comprising the following step:
chiral resolution of a mixture of the enantiomers (S)-(I) and (R)-(I) of Praziquanamine,

(S)-(I)

(R)-(I)

via precipitation of a diastereomeric salt formed by one of the enantiomers (S)-(I) or (R)-(I) with an enantiopure or enantioenriched chiral 2-aryl-propionic acid containing at least 14 C-atoms.

2. The method according to claim 1, wherein the 2-aryl-propionic acid is (S)-Naproxen or (S)-Ketoprofen.

3. The method according to claim 1, wherein the 2-aryl-propionic acid is (S)-Naproxen and the precipitated diastereomeric salt comprises (S)-Naproxen and (R)-Praziquanamine (R)-(I).

4. The method according to claim 3, wherein the diastereomeric salt is [(S)-Naproxen:(R)-Praziquanamine], which has a stoichiometry of X:1, wherein X is a real number between 1 and 3.

5. The method according to claim 4, wherein the method comprises following steps:
   separation [(S)-Naproxen:(R)-Praziquanamine] 2:1 salt via liquid/solid separation;
   isolating (R)-Praziquanamine from the [(S)-Naproxen:(R)-Praziquanamine] 2:1 salt via acidification of the reaction mixture and liquid/solid separation.

6. The method according to claim 5, wherein the acidification is achieved by an inorganic acid or an organic sulfonic acid or trifluoroacetic acid.

7. The method according to claim 1, wherein
   the 2-aryl-propionic acid is (S)-Naproxen and the precipitated diastereomeric salt comprises (S)-Naproxen and (R)-Praziquanamine (R)-(I);
   the diastereomeric salt is [(S)-Naproxen:(R)-Praziquanamine], which has a stoichiometry of X:1, wherein X is a real number between 1 and 3;
   and the method further comprises following steps:
      separating the diastereomeric salt [(S)-Naproxen:(R)-Praziquanamine] via liquid/solid separation;
      isolating (R)-Praziquanamine via acidification of the reaction mixture and liquid/solid separation.

8. A method for preparing enantiopure or enantiomerically enriched (R)-Praziquantel comprising the method according to claim 1 and following step:
   reacting (R)-Praziquanamine (R)-(I) with a cyclohexylcarboxylic acid compound.

9. The method according to claim 8, wherein the cyclohexylcarboxylic acid compound is cyclohexylcarboxylic acid chloride.

10. The method according to claim 9, wherein the reaction with cyclohexylcarboxylic acid chloride is performed in the presence of a biphasic solvent system, wherein one solvent is water.

11. A method for preparing enantiopure or enantiomerically enriched (R)-Praziquanacetamide comprising the following step:
    chiral resolution of a mixture of the enantiomers (S)-(II) and (R)-(II) of N-substituted Praziquandiamine (S)-(II)

(R)-(II)

via precipitation of a diastereomeric salt formed by one of the enantiomers (S)-(II) or (R)-(II) with an enantiopure or enantioenriched chiral 2-aryl-propionic acid containing at least 14 C-atoms, wherein $R^2$ denotes denotes tert.-butyloxycarbonyl, benzoyl, cyclohexanoyl or acetyl.

12. The method according to claim 11, wherein the 2-aryl-propionic acid is (S)-Naproxen or (S)-Ketoprofen.

13. The method according to claim 12, wherein the method comprises following steps:
    separating the diastereomeric salt via liquid/solid separation;
    isolating N-substituted (R)-Praziquandiamine from the diastereomeric salt via acidification of the reaction mixture and liquid/solid separation.

14. A method for preparing enantiopure or enantiomerically enriched (R)-Praziquantel comprising the method according to claim 11 and following steps:
    deprotecting the N-substituted (R)-Praziquandiamine (R)-(II);
    reacting unprotected (R)-Praziquandiamine obtained in a) with a reactive cyclohexylcarboxylic acid compound;
    cyclizing the carboxamide obtained in b) with chloroacetyl chloride.

15. The method according to claim 1, wherein the method further comprises following step:
    racemizing enantiomerically pure or enantiomerically enriched compound according formula (I')

(I')

wherein
in the presence of a base, and
$R^1$ denotes H, tert.-butyloxycarbonyl, benzoyl or acetyl.

16. The method according to claim 15, wherein the base is a tertiary alkali alkoxide.

17. The method according to claim 15, wherein:
    the base is a tertiary alkali alkoxide;
    the dipolar aprotic reaction medium is N-Methyl-2-pyrrolidone, dimethylformamide, dimethylsulfoxide, tetrahydrofuran, methyltetrahydrofuran, dioxane or a mixture thereof;
    the amount of base for the racemization is between 0.05 eq to 1.5 eq;
    the racemization is performed at a temperature between −50° C. and +40° C.

18. A diastereomeric salt comprising (R)-Praziquanamine and (S)-Naproxen or a solvate thereof or (R)-Praziquanacetamide and (S)-Naproxen or (S)-Ketoprofen or a solvate thereof.

19. The diastereomeric salt according to claim 18 comprising (R)-Praziquanacetamide and (S)-Naproxen or (S)-Ketoprofen or a solvate thereof.

20. A diastereomeric salt according to claim 18 comprising (R)-Praziquanamine and (S)-Naproxen or a solvate thereof.

* * * * *